United States Patent
Jackson et al.

(10) Patent No.: US 9,422,641 B2
(45) Date of Patent: Aug. 23, 2016

(54) FILAMENTS COMPRISING MICROFIBRILLAR CELLULOSE, FIBROUS NONWOVEN WEBS AND PROCESS FOR MAKING THE SAME

(71) Applicant: Kimberly-Clark Worldwide, Inc., Neenah, WI (US)

(72) Inventors: David M. Jackson, Alpharetta, GA (US); Christopher O. Luettgen, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 307 days.

(21) Appl. No.: 14/044,571

(22) Filed: Oct. 2, 2013

(65) Prior Publication Data

US 2014/0121622 A1    May 1, 2014

Related U.S. Application Data

(60) Provisional application No. 61/720,510, filed on Oct. 31, 2012.

(51) Int. Cl.
*A61F 13/15* (2006.01)
*B29B 9/00* (2006.01)
(Continued)

(52) U.S. Cl.
CPC ............... *D01F 2/00* (2013.01); *A61L 15/425* (2013.01); *A61L 15/60* (2013.01); *D01F 1/02* (2013.01);
(Continued)

(58) Field of Classification Search
CPC ............ A61F 13/156; A61F 13/15617; A61F 13/15626; A61F 13/15634; A61F 13/00991; A01B 12/006

USPC .......... 604/367, 366, 377, 375, 374; 264/103, 264/6, 122
See application file for complete search history.

(56) References Cited

U.S. PATENT DOCUMENTS

| | | | |
|---|---|---|---|
| 4,502,867 | A | 3/1985 | Reinhardt |
| 5,932,158 | A | 8/1999 | Boerstoel et al. |

(Continued)

FOREIGN PATENT DOCUMENTS

| | | |
|---|---|---|
| EP | 0 964 093 B1 | 8/2007 |
| GB | 1 020 169 A | 2/1966 |

(Continued)

OTHER PUBLICATIONS

Chinga-Carrasco, Gary, "Cellulose Fibres, Nanofibrils and Microfibrils: The Morphological Sequence of Microfibrillar Cellulose (MFC) Components from a Plant Physiology and Fibre Technology Point of View," Nanoscale Research Letters 2011; vol. 6, No. 1, p. 417, published online Jun. 13, 2011, at "http://www.nanoscalereslett.com/content/6/1/417", pp. 1-7.

*Primary Examiner* — Jacqueline Stephens

(57) ABSTRACT

Disclosed herein is a cellulosic textile filament made from microfibrillar cellulose fibers and a thickening agent as well as the precursor dope for forming such filaments, nonwoven webs made from such cellulosic textile filaments and the process for forming such filaments and nonwoven webs including such filaments. One of the advantages of these filaments is the eco-sensitive way in which they are made as they utilize a water-based dope that does not require any chemical solvents unlike other processes such as those used to make Lyocell fibers. In addition, the process does not involve any washing or extraction steps and it employs a cellulosic fiber source that is broadly based and renewable.

6 Claims, 3 Drawing Sheets

(51) Int. Cl.
*D02G 1/20* (2006.01)
*D04H 1/00* (2006.01)
*D01F 2/00* (2006.01)
*D01F 1/02* (2006.01)
*A61L 15/42* (2006.01)
*A61L 15/60* (2006.01)
*A61F 13/00* (2006.01)

(52) U.S. Cl.
CPC ..... *A61F 13/00991* (2013.01); *A61F 13/15617* (2013.01); *A61F 13/15626* (2013.01); *A61F 13/15634* (2013.01); *Y10T 428/298* (2015.01)

(56) References Cited

U.S. PATENT DOCUMENTS

| | | |
|---|---|---|
| 6,235,392 B1 | 5/2001 | Luo et al. |
| 6,267,898 B1 | 7/2001 | Fukuda et al. |
| 6,306,334 B1 | 10/2001 | Luo et al. |
| 6,540,853 B1 | 4/2003 | Suzuki et al. |
| 2005/0070703 A1 | 3/2005 | Muller et al. |
| 2006/0246285 A1 | 11/2006 | Schmidtbauer et al. |
| 2011/0028608 A1 | 2/2011 | Innerlohinger et al. |
| 2011/0124258 A1 | 5/2011 | White et al. |
| 2011/0263840 A1 | 10/2011 | Turner et al. |
| 2012/0052036 A1 | 3/2012 | Glenn, Jr. et al. |
| 2013/0012857 A1* | 1/2013 | Flynn ................ A61F 13/00012 602/43 |

FOREIGN PATENT DOCUMENTS

| | | |
|---|---|---|
| JP | 3702625 B2 | 10/2005 |
| WO | WO 97/30090 A1 | 8/1997 |
| WO | WO 99/47733 A1 | 9/1999 |
| WO | WO 01/81664 A1 | 11/2001 |
| WO | WO 2007/124521 A1 | 11/2007 |
| WO | WO 2010/135234 A2 | 11/2010 |

* cited by examiner

FILAMENTS COMPRISING MICROFIBRILLAR CELLULOSE, FIBROUS NONWOVEN WEBS AND PROCESS FOR MAKING THE SAME

This application claims the benefit of priority from U.S. Provisional Application No. 61/720,510 filed on Oct. 31, 2012.

BACKGROUND OF THE INVENTION

The present invention relates to the field of the manufacture and use of cellulose filaments from renewable resources as well as products including such filaments.

Energy and resource conservation is an ever growing area of focus. Energy costs continue to rise and many material sources such as petroleum-based materials are under constant cost and availability concerns. One area in which this is particularly true is with disposable and semi-durable goods, especially in the area of consumer products used for personal, home and commercial applications.

Today's consumer daily routine often involves the use of products that are either single use products or products that are only used several times before being discarded. Non-limiting examples of such products include, but are not limited to, personal care absorbent articles, hygiene-related products, and cleaning products for home, business and commercial applications. Examples of personal care absorbent articles include, but are not limited to, diapers, diaper pants, training pants, feminine hygiene products, adult incontinence devices, wet and dry wipers, bandages and the like. Hygiene-related products include, but are not limited to, cleansing wipes, make-up and beauty wipes and pads. Cleaning products include, but are not limited to, household wipes and towels, paper towels, mop covers, etc.

Many of the foregoing and other products utilize petroleum-based materials such as polyolefin and other polymer-based filaments which are employed in the manufacture of fibrous nonwoven webs which are used to absorb and or dispense fluids. For example, many of the layers in personal care absorbent articles are made from polymer-based fibrous nonwovens.

An effort has been ongoing to make such filaments and nonwovens from sustainable resources and to move away from more petroleum-based products. One area has been in connection with the manufacture of such filaments and nonwovens from renewable raw materials which are cellulose-based. One well known method is referred to as the Lyocell process which is one of many examples of processes which require chemically-based solvents (N-methylmorpholine N-oxide) to dissolve the cellulose to permit it to be formed into a fiber. Once the fiber is formed other chemicals such as amine oxide is used to set the fiber after which the fibers have to be washed in water to remove the formation chemicals. Obviously this involves many processing steps, the use of additional chemicals that cost more money to use, extract and recycle and well as potential environmental issues concerning the use and disposal of the chemicals used in the process. It would therefore be desirable to have a more simplified process that would involve fewer steps, the use of fewer chemicals and therefore a lower cost in the context of manufacture. The present invention is directed to such an effort.

SUMMARY OF THE INVENTION

Disclosed herein is a cellulosic textile filament utilizing microfibrillar cellulose that is made with very few chemical additives from a water-based process that is simplified in its components and process steps for manufacture. Unlike other processes such as the aforementioned Lyocell process, there is no need to use chemicals such as N-methylmorpholine N-oxide to dissolve the cellulosic source in order to make an extrudable fiber dope which, after formation must be subject to the use of additional chemicals and subsequent extraction and/or washing processes to remove the chemicals used in the initial part of the fiber-forming process. Thus the process of the present invention is more of a physical process than a chemical/dissolution process as is the case with, for example, the Lyocell process. In addition, the microfibrillar cellulose can be made from an almost infinite number of cellulosic plant resources all of which are renewable and in some cases the byproduct of other cellulose-based processes. As a result, filaments, fibrous nonwoven webs and end products can be made from a totally renewable resource with fewer steps and fewer chemicals. This is turn means that the materials generated by way of the present invention may be suitable candidates for replacement in a number of products which currently rely upon fibers and fibrous nonwoven webs which are based on petroleum and other non-renewable bases.

The filaments of the present invention are made from a cellulosic textile filament precursor dope which is comprised, based upon the total weight of the precursor dope, from about 7 to about 20 weight percent of microfibrillar cellulose fibers, about 0.2 to about 3 weight percent of a thickening agent and about 75 to about 95 weight percent of a water-based solvent. The microfibrillar cellulose fibers are dispersed in the water-based solvent while the thickening agent is dissolved in the solvent. The precursor dope should have a dynamic viscosity ranging from about 400 to about 3000 Pascal seconds at a shear rate of 100 reciprocal seconds.

In certain embodiments, other components including, but not limited to, binding agents, both physical and chemical, may be added to the precursor dope to improve the integrity of the resultant filaments formed from the precursor dope.

Once formed, in one embodiment the cellulosic textile filament can comprise, based upon the total dry weight of the filament, from about 80 to about 99.5 weight percent of microfibrillar cellulose fibers and about 20 to about 0.5 weight percent of a thickening agent. When calculating dry percentages in the formed filaments, the percentages are based upon the total weight of the dry ingredients and exclude any residual moisture. Thus, for example, if a filament or sample has a total weight of 110 grams including 80 grams of microfibrillar cellulose, 20 grams of a thickening agent and 10 grams of residual moisture, the dry weight percentages would be 80 percent by weight microfibrillar cellulose and 20 percent by weight thickening agent.

In an alternate embodiment the cellulosic textile filament can comprise, based upon the total dry weight of the filament, of from about 75 to about 99 weight percent microfibrillar fibers, from about 20 to about 0.5 weight percent of a thickening agent and from 0.5 to about 5 percent of other components. One example of another component is a binding agent.

The filaments so formed will generally have a diameter in a dried state of between about 5 and about 50 microns. The lengths of the filaments can be varied to meet the particular end need. Filaments can be formed of a staple fiber length which is typically between about 6 and about 50 millimeters but longer more continuous filaments can be formed depending upon the filament extrusion process being used and so filaments which are more continuous in nature such as are found in conjunction with meltblown and spunbond forming processes are also contemplated to be within the scope of the present invention. Further, filaments with much smaller lengths, below those typically used for staple fiber purposes may be formed for yet other uses.

Typically, the thickening agent will have a viscosity average molecular weight (Mv) of between about 200,000 and about 2,000,000 which can be determined by standard methods used in the industry depending on the material in question. While a broad number of thickening agents may be suitable for use in the formation of the filaments, the thickening agent may be selected from the group consisting of polyethylene oxide, poly (vinyl pyrrolidone), nanocrystalline cellulose, hemicellulose and nanostarch.

To form a filament and resultant fibrous nonwoven web according to the present invention, a water-based dispersion of the precursor dope as described above must first be formed and then mixed to a viscosity of about 400 to about 3000 Paschal seconds (Pa s) at a shear rate of 100 reciprocal seconds ($s^{-1}$). Generally, for extrusion into filaments, the shear rate during the spinning process will be between about 50 and about 200 reciprocal seconds. Once within the viscosity and shear rate ranges stated above, the precursor dope could be extruded using a filament die or otherwise formed into a filament on a forming surface and then dried. The thus formed filaments may then be subjected to other processing steps such as cutting or chopping into smaller filament lengths as well as crimping to increase their bulk. With larger multi-extruder heads or other types of extrusion orifices and devices, the precursor dope could be extruded into a plurality of filaments which are then deposited in a random pattern onto a surface to form a fibrous nonwoven web which is then dried and if desired, subjected to further processing. For example, either prior to, in conjunction with or after the drying process, the fibrous nonwoven web can be subjected to bonding and/or entanglement processes to further improve the strength and integrity of the overall web. In one form of the bonding process, either or both smooth and embossed calender rolls may be used to change the surface texture and appearance of the fibrous nonwoven web so formed or to impart embossed designs to change the aesthetic properties of the nonwoven or to give it more three-dimensional character and bulk. Due to the affinity of the formed filaments to water, it may be more suitable to use entanglement processes that are non-water-based such as needling or air entanglement processes. However, it is possible to add small amounts of water, as by a water spray, to the formed filaments/nonwovens followed by further compaction/embossing with embossing/calendaring rolls. Generally, the amount of water added should be no more than five percent by weight, based upon the weight of the water and filament/nonwoven as compared to the filament/nonwoven weight prior to the addition of the water.

Once the filaments have been formed, it is believed that their internal strength is based, at least in part, on hydrogen bonds within the filaments, themselves. It should be recognized, however, that this initial integrity can be increased through other treatments such as by surface coating the filaments or resultant fibrous nonwoven web with additional binding agents such as glues and polymer coatings.

The resultant filaments can be used in a wide variety of applications. They can be used alone or they can be mixed with other fibers (both natural and synthetic) to form fibrous nonwoven webs with additional properties. In addition, other components can be added to the filaments as part of the precursor dope or after formation of the filaments either before or after the filaments have been fully dried. For example, superabsorbent material in either fiber or particle form may be added to or with the filaments to form high capacity structures such as fibrous nonwoven webs which may function to absorb body fluids such as urine, menses and fecal matter. Other components such as dyes, pigments, treatments and activated particulate matter may be added to either the precursor dope or the filaments once formed. Treatments that may be added to the filaments either as part of the precursor dope or the formed filaments may include, but are not limited to, fire retardants, polymer coatings, and surface tension modifiers to mention just a few.

Fibrous nonwoven webs incorporating cellulosic textile filaments according to the present invention may be used alone or in combination with other materials and layers to form multifunction structures, laminates and products. They may be placed adjacent to or laminated with other fibrous nonwoven materials, film layers and combinations of the same. In this regard, the fibrous nonwoven webs incorporating or formed from cellulosic textile filaments according to the present invention may be bonded or entangled with other materials or substrates such as other fibrous nonwoven webs and other materials.

Absorbent articles including personal care absorbent articles are one product area where the filaments themselves or fibrous nonwoven webs containing such filaments may be used as all or at least a portion of such absorbent articles. Examples of such absorbent articles include but are not limited to diapers, diaper pants, incontinence devices for both adults and children, feminine hygiene products including sanitary napkins, pantiliners and tampons, as well as bandages, wipes, bed pads, nursing pads, and other paper-based products. The filaments and fibrous nonwoven webs containing such filaments may also be used to form all or a portion of other products including, but not limited to, hygiene-related products such as cleansing wipes, make-up and beauty wipes and pads as well as cleaning products such as household wipes and towels, paper towels, mop covers, etc. In addition, the filaments and fibrous nonwoven webs containing such filaments may also be used to form all or a portion of other products such as wipes and disposable apparel for use in a wide variety of applications including industrial, clean room and health care related applications.

DETAILED DESCRIPTION OF THE INVENTION

Material Components

Figure 1:
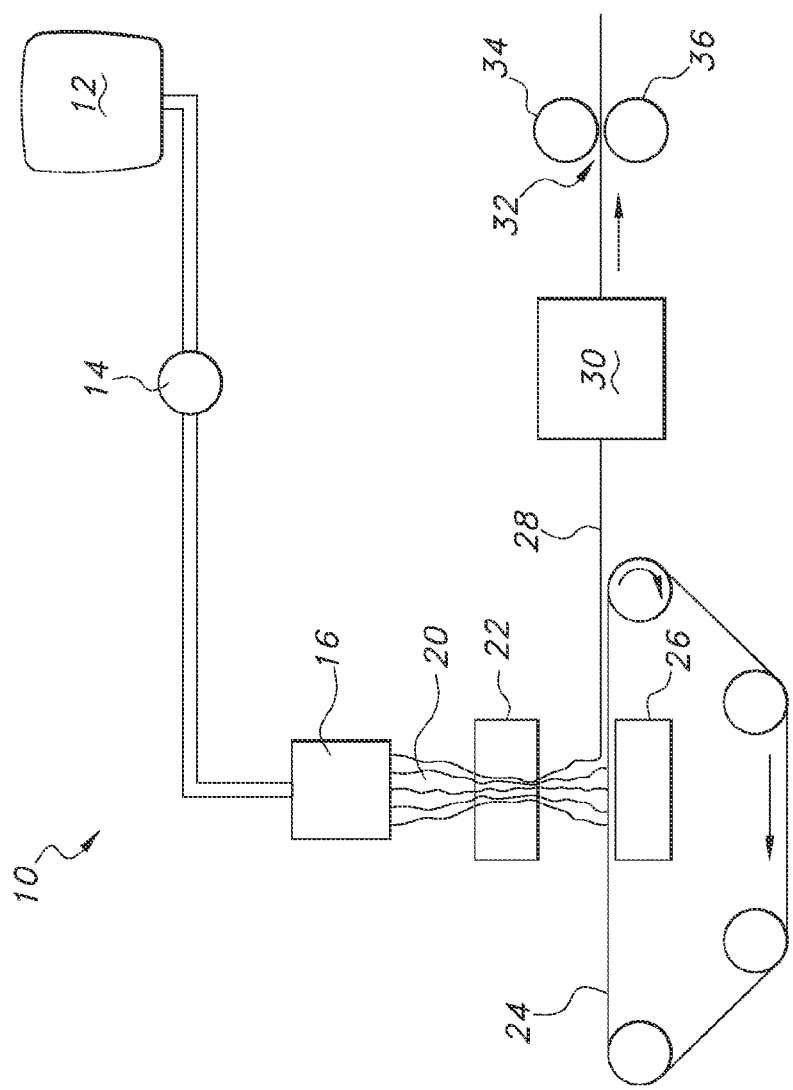
FIG. 1 is a proposed commercial grade process that could be used to form cellulosic textile filaments and fibrous nonwoven webs according to the present invention.

The cellulosic textile filament precursor dope has three main components, a solvent, microfibrillar cellulose and a thickening agent. Other components may be included to vary the properties of the filaments and resultant end products as will be explained in further detail below.

Solvent

The solvent used to make the cellulosic precursor dope is water or at a minimum water-based meaning that it essentially water and in any event at least 90 percent by volume of the solvent is composed of water. An important advantage of the present invention is its low cost approach and the fact that there is no need to use additional components beyond the microfibrillar cellulose and a thickening agent to form the spinning dope, a filament and the resultant fibrous nonwoven webs and end products. As a result, no chemical-based solvents are needed to dissolve the cellulose and no extraction, washing or other chemical removal processes must be used to generate the microfibrillar cellulose filaments and nonwovens as is the case with other well-known processes such as the Lyocell process. If desired, the water source may be purified and/or distilled but this is not necessary for the process and resultant material to work.

As shown by the examples below, the process may be carried out at room temperature but if desired, the water-based solvent and the resultant cellulosic filament precursor dope may be heated to an elevated temperature. Whether heat is added to the process in some cases will depend on the thickening agent being used. Also, the range of temperatures used will depend on the pressures being used to extrude the filaments. At normal atmospheric pressure, temperatures must be below the boiling point of water so as to not cause bubble formation which could disrupt the filament formation. As a result, temperatures will generally be below about 200 degrees Fahrenheit (93° C.). However, as extrusion pressures increase, the temperature of the precursor dope and the water contained therein may be elevated to temperatures above 212 degrees Fahrenheit (100° C.) but generally, at normal sea level/STP conditions, the temperatures should remain below about 210 degrees Fahrenheit (99° C.) so the water does not flash off as steam and disrupt the filament formation.

Typically the water-based solvent will be present in the water-based dispersion precursor dope in a weight percent of about 75 to about 95 weight percent based upon the total weight of the precursor dope including the dry and wet ingredients.

Microfibrillar Cellulose

The main dry component of the cellulosic textile filaments of the present invention is microfibrillar or microfibrillated cellulose also referred to as "MFC". Microfibrillar cellulose is a form of cellulose generated by applying high shear forces to cellulosic fibers to yield cellulose fibrils with a lateral dimension or diameter in the range of about 10 to about 100 nanometers (nm) and lengths which are generally in the micrometer scale.

One of the advantages of the present invention is that the cellulosic sources available to form the microfibrillar cellulose for the present invention are almost infinite. Generally, any cellulosic source which can, with proper processing, yield microfibrillated cellulose fibers of the size mentioned above, can become a source of such MFC for the present invention. Some examples of cellulose sources include, but are not limited to, wood pulp, algae, trees, grasses, Kenaf, hemp, jute, bamboo, and microbial cellulose.

Numerous articles and literature are available on microfibrillar cellulose, its sources and production. See for example, Turbak A, Snyder F, Sandberg K (1983) *Microfibrillated cellulose: a new cellulose product: properties, uses, and commercial potential*. J Appl Polym Sci Appl Polym Symp 37:815-827 which is incorporated herein by reference in its entirety. See also Chinga-Carrasco, Gary (Jun. 13, 2011), *Cellulose fibres, nanofibrils and microfibrils: The morphological sequence of microfibrillar cellulose components from a plant physiology and fibre technology point of view*, Nanoscale Res Lett. 2011; 6(1): 417. published online 2011 Jun. 13. doi: 10.1186/1556-276X-6-417PMCID: PMC3211513 which is incorporated herein by reference in its entirety.

Microfibrillar cellulose can be made, for example, by mechanical disintegration of cellulose fibers. To accomplish this, first, a cellulose source such as softwood pulp is Willey milled and passed through a 0.50 millimeter sieve. Willey mills, such as the Mini model, are available from Thomas Scientific in Swedesboro, N.J. After the cellulose has been milled, it is next refined using a PFI mill for 3×10k revolutions and then diluted with water to approximately 0.2 percent solids, based upon the total weight of the cellulose source and the water, and passed through a DeBee bench top homogenizer from BEE International Inc. of South Easton, Mass. three times at 22,000 pounds per square inch ($1.52 \times 10^8$ Paschals). Finally, the homogenized material is centrifuged with a Beckman Avanti J-E centrifuge at 12,000 revolutions per minute (rpm) for thirty minutes to obtain the microfibrillated cellulose. (For more information on PFI mills see TAPPI test method T 248 sp-08 which is incorporated herein by reference in its entirety.)

Typically the microfibrillar cellulose will be present in the water-based dispersion precursor dope in a weight percent of about 7 to about 20 weight percent based upon the total weight of the precursor dope including the dry and wet ingredients. In the finished, dry filament, the microfibrillar cellulose content will range between about 80 and about 99.5 percent by weight based upon the total dry weight of the filament.

For the examples and testing set forth below, microfibrillar cellulose was obtained from the Georgia Institute of Technology in Atlanta, Ga. The obtained microfibrillar cellulose once formed was centrifuged with a Beckman Avanti J-E centrifuge at 12,000 rpm for 30 minutes to yield a mud-like microfibrillar cellulose product having a weight of 109.1 grams and an average solids content of 15.2 percent.

Anticipated advantages of filaments formed from microfibrillar cellulose are that the so-produced filaments will have similar strength to polypropylene fibers of similar size with less elongation. Also, filaments formed from microfibrillar cellulose can sustain higher drying and process temperatures than polymer-based fibers such as polyolefins including polypropylene. Unlike polyolefin-based nonwoven webs, ones made from microfibrillar cellulose filaments are inherently wettable and have higher absorbent capabilities.

Thickening Agents

To change the dynamic viscosity (also referred to as the complex viscosity) of the microfibrillar cellulose dispersed in the water-based solvent, thickening agents may be employed and dissolved in the water-based dispersion precursor dope to assist in the extrusion and filament forming process. Suitable thickening agents will have to be able to increase the viscosity of the water-based dispersion of microfibrillar cellulose. Typically, the thickening agent will cause the water-based dispersion of microfibrillar cellulose to have a dynamic viscosity between about 400 and about 3000 Pascal seconds (Pa s) at a shear rate of 100 reciprocal seconds ($s^{-1}$), more specifically between about 800 and about 1250 Pa s @ a shear rate of 100 $s^{-1}$.

Complex viscosity follows Newton's law and is written as $\tau(t)=\eta^* d\gamma/dt$. The star is used to indicate that the viscosity is measured in an oscillatory test rather than the normal steady state shear rate test, for example, in a capillary rheology measurement. According to the Cox/Merz rule, $\eta(d\gamma/dt)=|\eta^*(\omega)|$ if the values of $d\gamma/dt(s^{-1})$ and $\omega(s^{-1})$ are the same. So complex viscosity can be used to set the processing conditions.

Complex viscosity is a frequency-dependent viscosity function determined in response to a forced sinusoidal oscillation of shear stress. It is obtained by dividing the complex modulus by the angular frequency ($|\eta^*|=|G^*|/\omega$) and is used to study the visco-elastic nature of a fluid. When a visco-elastic fluid is stressed in a sinusoidal manner, the resulting sinusoidal shear rate function is somewhere between, a completely in-phase and out-of-phase response. The in-phase component is the real part of the complex viscosity ($\eta'=G''/\omega$), also known as the dynamic viscosity and represents the viscous behavior and the imaginary part of the complex viscosity ($\eta''=G'/\omega$) represents the elastic behavior. The complex viscosity function is expressed as the difference between the in-phase viscosity and the out-of-phase viscosity or the imaginary components of the complex viscosity, $\eta^*=\eta'-i\eta''$.

The dynamic or complex viscosity can be measured using an Anton Paar Model Physica MCR 301 rheometer from Anton Paar GmbH of Graz, Austria at room temperature (70° F./21° C.) conditions. Determination of the complex viscosity of a cellulosic precursor dope can be determined in accordance with the manual for this apparatus which is incorporated herein by reference in its entirety. The determination of the viscosity versus shear rate for sample 10 of the examples is shown in Table 3 and FIG. 3 of the drawings.

Specific examples of thickening agents include, but are not limited to, polyethylene oxide (PEO), polyvinylpyrrolidone, nanocrystalline cellulose, hemicellulose and nanostarch. Examples of PEO include those available from Sigma-Aldrich Co, LLC of Saint Louis, Mo. including grade 372781 PEO with a viscosity average molecular weight (Mv) of 1,000,000, grade 182028 with a viscosity average molecular weight (Mv) of 600,000 and grade 181994 with a viscosity average molecular weight (Mv) of 200,000. An example of a suitable polyvinylpyrrolidone is grade 437190 also from Sigma-Aldrich with a weight average molecular weight (Mw) of 1,300,000. Nanocrystalline cellulose is available from CelluForce, Inc. of Montreal, Canada. As to the molecular weight of the thickening agent it should be noted that some molecular weights are reported by the manufacturers and suppliers as number average molecular weights (Mn), weight average molecular weights (Mw) and viscosity average molecular weights (Mv). Thus, the appropriate version of the molecular weight should be determined by standard methods as used by the industry for the particular material in question.

Other examples of thickening agents include, but are not limited to, maltodextrin, soy protein isolate, carboxymethylcellulose, alginic acid, gelatin, textured soy protein, guar gum, xanthan gum, modified corn starch, carrageenan, sugar, ester, calcium alginate, pectic, konjac, liquid glucose and sodium triphosphate. Further, it should be appreciated that this list is not exhaustive and other thickening agents are also contemplated to be within the scope of the present invention provided they are compatible with the other components of the water-based dispersion precursor dope and the process and equipment parameters chosen to form the filaments according to the present invention.

Generally, thickening agents which are suitable with the present invention will have viscosity average molecular weights (Mv) up to about 2,000,000. Generally, the viscosity average molecular weight of the thickening agent will range between about 200,000 and about 2,000,000 and more specifically between about 500,000 and about 1,000,000 though other molecular weights may be used depending on the particular end-use application. The amount of thickening agent that will be used will typically range between about 0.2 and about 3.0 weight percent based upon the total weight of the water-based dispersion precursor dope including the weights of the solvent, the microfibrillar cellulose, the thickening agent and any other additives or components. The end result of the type and quantity of such thickening agents used in the precursor dope is the desire to yield a precursor dope that falls within the above-stated viscosity ranges so that suitable filaments may be extruded by the particular equipment being used.

In the finished, dry filament, the thickening agent content will range between about 20 and about 0.5 percent by weight based upon the total dry weight of the filament.

Other Components

While a solvent, thickening agent and microfibrillar cellulose are the core components of both the precursor dope and end-use filaments and fibrous nonwoven webs, other components may be included depending upon the particular end-use application. Other components include, but are not limited to, water-based binding agents. Di-aldehydes are on example of binding agents that may be used with the present invention. Typically the binding agent being used should be designed to not prematurely crosslink at a point where it interferes with the formation of the dope or filament forming process. As a result, it is desirable to use binding agents that can be activated or facilitated in their binding through the use of additional heat such as can be applied during a drying process after the filaments have been formed. One example in this regard is an acrylic latex binder which can be accelerated with heated air at temperatures of about 300° F./149° C.

When other components are added to the filament precursor dope, it is generally desirable to add them in an amount such that finished, dry filament will have, based upon the total dry weight of the filament, from about 75 to about 99 weight percent microfibrillar cellulose fibers, from about 20 to about 0.5 weight percent of a thickening agent and from 0.5 to about 5 percent of other components.

Equipment and Process

The cellulosic textile precursor dope materials and filaments set forth in the examples below were made using bench scale equipment. The microfibrillar cellulose, thickening agent and water were mixed in the prescribed proportions on a weight percent basis based upon the total weight of all wet and dry components in a 150 milliliter container and stirred by hand using a glass stirring rod to the highest level of uniformity and dispersion possible to form the precursor dope. Typically this took approximately 60 to 120 minutes of repeated intervals of stirring for one to two minutes and letting the sample rest for five to ten minutes until an acceptably uniform dispersion was obtained (visually no lumps). The precursor dope was then poured into the open end of a common 25 milliliter capacity disposable plastic syringe which had no needle. The plunger was replaced and the air removed. The exit orifice on the syringe from which the dope was extruded had an approximate diameter of one millimeter. The syringe was held by hand at a 45 degree angle to a horizontal laboratory bench surface upon which there was placed a silicone-treated paper which formed the horizontal forming surface upon which the dope was deposited. The tip of the syringe was held approximately two centimeters above the forming surface.

The filaments were extruded from the handheld syringe while the syringe was drawn backwards as the precursor dope was extruded from the syringe tip by depressing the plunger into the syringe housing. Filament lengths were in the range of approximately 300 millimeters. Initial wet diameters of the filaments were approximately one millimeter. The filaments were allowed to air dry at room temperature overnight. Once dried, the filaments exhibited shrinkage in their diameters. Dry diameters were approximately 0.25 millimeters. All portions of the above-described process were performed at room temperature (75° F./21° C.). Visual observation of the filaments showed them to be well formed and the filaments exhibited good tensile strength when pulled by hand.

Due to the low solids content of the water-based dispersion textile filament precursor dope, shrinkage of the newly formed filament and thus reduction in filament diameter must be factored into the process parameters. For example, if a 30 micron diameter filament is desired once the filament has dried from a precursor dope having a solids content of approximately ten percent, the initial filament diameter will have to be approximately 95 microns to compensate for the shrinkage. This relationship is linear and so, for example, at the same ten percent solids content a 10 micron dry filament will require an approximate 32 micron wet filament diameter. In addition, draw down of the filament as it is extruded must also be taken into consideration. Typically it should be assumed that the draw down in filament diameter in a commercial process will be in the range of 50 to 80 percent. Thus, if a dry filament diameter of 5 to 50 microns is desired, utilizing an approximate 15 percent solids precursor dope, it is anticipated that the wet filament diameter will have to be in the range of 70 to 100 microns. As a result, it is also anticipated that the extrusion equipment will have to utilize extrusion openings or orifices with diameters in the range of 70 to 100 microns to yield dry, finished filaments with filament diameters in the 5 to 50 micron range though this can be adjusted accordingly depending on the viscosity of the water-based dispersion precursor dope, the amount of draw of the filaments as they are extruded, the forming height of the extrusion orifices from the forming surface, the flow rate of the precursor dope from the orifices, the draw of the filaments and the speed of the forming surface.

As described in the examples, the microfibrillar cellulose filaments were made using bench scale equipment but it is anticipated that conventional fiber extrusion equipment can be used including, for example, equipment utilized in making cellulosic-based fibers and nonwovens according to the Lycocell process. See, for example, U.S. Pat. Nos. 6,306,334 and 6,235,392 both to Luo et al.; U.S. Patent Application Publication No. 2011/0124258 to White et al. and WO 01/81664 to Luo et al., each of which is incorporated herein by reference in its entirety. This type of equipment can be utilized to mix and spin the microfibrillar cellulose filaments according to the present invention with the difference being that 1) no chemicals need be added to the solvent used to dissolve the cellulose, 2) minimal gas or mechanical stretching need necessarily be used due to the tenacity of the filaments being formed, 3) no insolubilizing step need be used and lastly, 4) no washing or other chemical extraction step need be implemented to yield the resultant filaments. FIG. 1 illustrates a schematic diagram of a prophetic process which could be used to form the filaments and fibrous nonwoven webs according to the present invention.

Turning to FIG. 1 there is shown a process and equipment 10 according to the present invention including a precursor dope tank 12, a spin pump 14 and an extrusion die 16. The precursor dope is placed in the dope tank 12 and pumped to the extrusion die 16 by way of the spin pump 14. The precursor dope exits the extrusion die 16 in the form of filaments 20 which are deposited onto a forming surface 24. If desired, an optional drawing unit 22 can be used between the extrusion die 16 and the forming surface 24 to further draw and attenuate the filaments as they exit the extrusion die 16 and before they are deposited onto the forming surface 24. A vacuum assist 26 may be used to facilitate the deposition of the filaments down onto the forming surface 24 to form a fibrous nonwoven web 28. After the web 28 is formed, it may be subjected to a drying step via a dryer 30 and, if desired, further processing steps as mentioned above including, but not limited to, such steps as calendering and/or embossing by passing the nonwoven web 28 through the nip 32 of a pair of calender/embossing rolls 34 and 36 either or both before and after the dryer 30.

Figure 2:
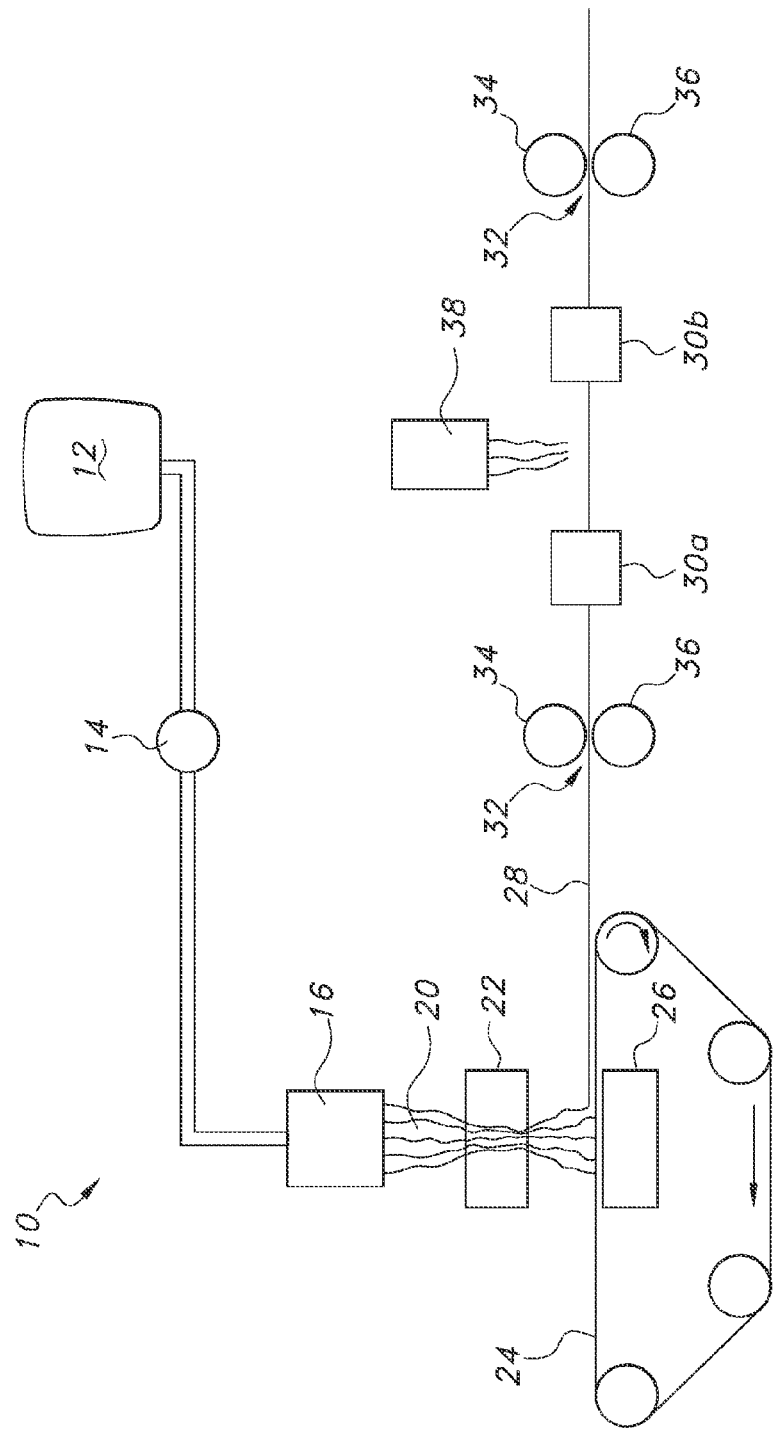
FIG. 2 is an alternate proposed commercial grade process that could be used to form cellulosic textile filaments and fibrous nonwoven webs according to the present invention.

A possible alternate embodiment of a process for forming cellulosic filaments according to the present invention is shown in FIG. 2 of the drawings. In this embodiment, in which like numerals represent like elements, a two stage drying process may be employed wherein the newly-formed fibrous nonwoven web 28 is subjected to a first drying step via dryer 30a after which the web 28 is subjected to a water spray 38 followed by a second drying step via dryer 30b. Typically water add-on would be no more than about five percent by weight based upon the weight of the fibrous nonwoven web and the water.

EXAMPLES

The MFC concentrate before it is let down is a very thick paste. As a result, water must be added in increasing amounts to the MFC to generate a precursor of suitable viscosity. Once this is done, specified amounts of PEO thickening agent can be added. If need be, additional water can be added during the hand mixing process to yield a precursor dope with suitable viscosity after which the dope can be extruded by hand with the above described syringe. Satisfactory dopes were made at 5.0-7.5 weight percent microfibrillar cellulose and 1.0-2.3 weight percent PEO based on the total weight of all wet and dry ingredients in the dope. Filaments were produced by extruding the dope at room temperature, from a simple syringe, and allowing them to air dry. Filaments so produced were quite strong.

A total of ten samples of microfibrillar cellulose precursor dope were made and formed into filaments. The data regarding these ten samples are set forth in Table 1 below. Three components were used to form the microfibrillar cellulose precursor dope including the microfibrillar cellulose, a thickening agent and tap water as a solvent. The microfibrillar cellulose was obtained from Georgia Institute of Technology in Atlanta, Ga. The microfibrillar cellulose sample material had an oven-dried weight of 16.6 grams. The homogenized microfibrillar cellulose (~0.16%) was centrifuged with a Beckman Avanti J-E centrifuge at 12000 rpm for 30 minutes, after which a mud-like microfibrillar cellulose product was acquired. The solid contents within the centrifuged microfibrillar cellulose sample were not uniform as there was a graduation of the solid content from 12.52% at the top of the sample to 19.35% at the bottom of the sample with the average solid content is 15.2%. The sample weighed 109.1 g, and so multiplying the weight in grams by the solids content (109.1 g×0.152) yielded an oven dried weight of 16.6 g for the microfibrillar cellulose.

The thickening agents used in the samples were the three previously identified polyethylene oxides (PEO) available from Sigma-Aldrich Co., LLC of Saint Louis, Mo. The thickening agent referred to as "Low" in Table 1 below was grade 181994 with a viscosity average molecular weight (Mv) of 200,000. The thickening agent identified as "Medium" in Table 1 below was grade 182028 with a viscosity average molecular weight (Mv) of 600,000 and the thickening agent identified as "High" was grade 372781 PEO with a viscosity average molecular weight (Mv) of 1,000,000.

Samples 1, 2 and 3 contained no MFC. The purpose of these samples was to determine the effect of the amount and type (molecular weight) of thickening agent on the viscosity of the water solvent. The desire was to create a precursor with a molasses-like viscosity. In sample 4, MFC only was added to the water, again to determine a subjective viscosity. In samples 5 and 6, varying amounts of MFC and medium molecular weight PEO were added to water. The purpose here was to focus on determining a blend ratio between the MFC and the medium molecular weight PEO grade.

In samples 7 and 8, varying amounts of MFC were added to water but no thickening agents were used to observe the level of dispersion of the MFC in the solvent. In samples 9, MFC and medium molecular weight PEO were added to water in an effort to optimize the ratios of components and to determine the mixing order. It was found that the preferred method was to add the MFC to the water first and then add in the thickening agent.

Figure 3:
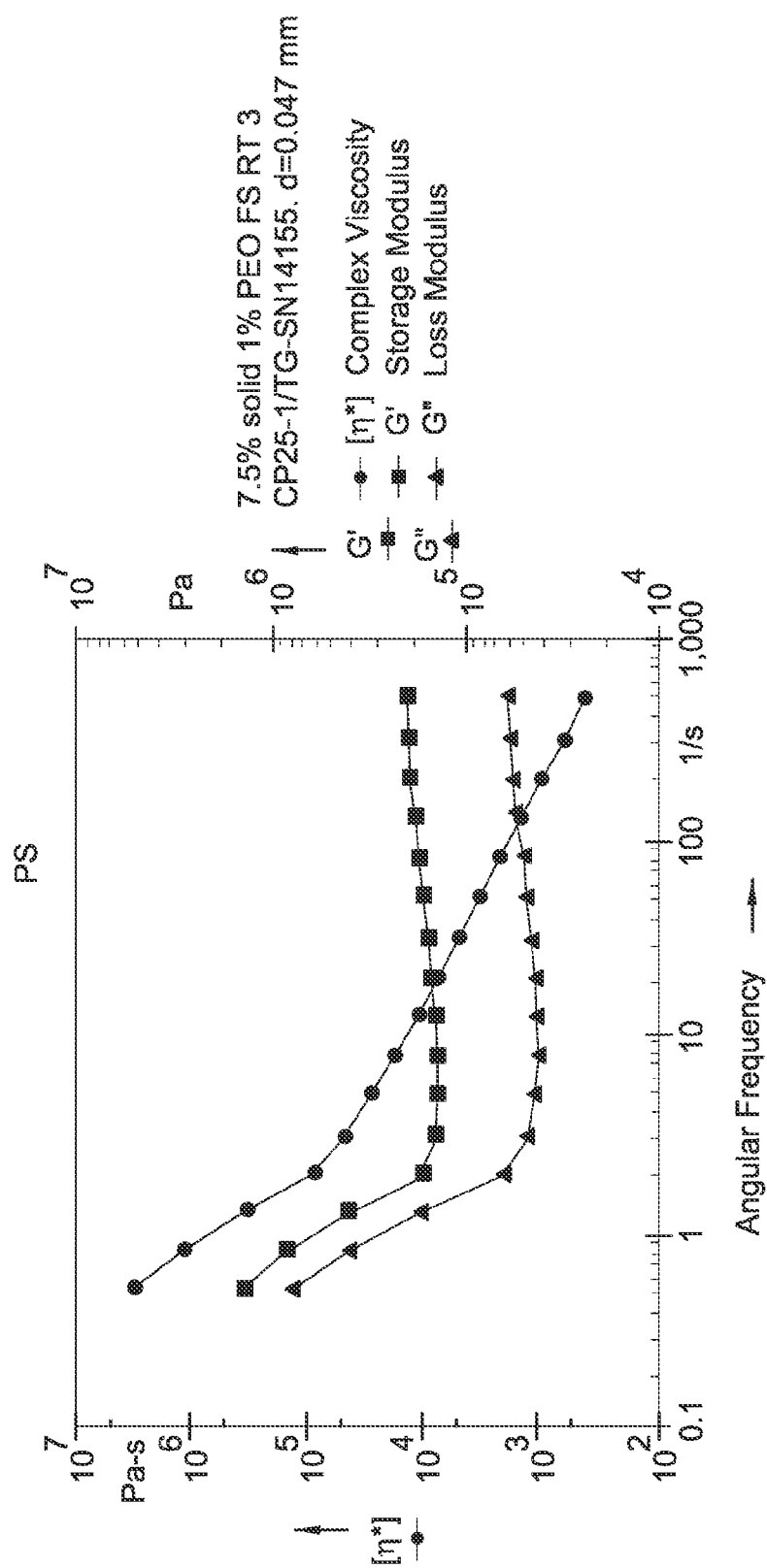
FIG. 3 is a plot showing the complex or dynamic viscosity of a cellulosic filament precursor dope according to the present invention based upon sample number 10 in the examples. The plot shows the viscosity in Paschal seconds (Pa s) as a function of the angular frequency (shear rate) in reciprocal seconds.

Finally, in sample 10 MFC and high molecular weight PEO were added to water in an effort to optimize the mix using the higher molecular weight PEO as, from a commercial standpoint, it is more desirable to use a higher molecular weight thickening agent so as to minimize the concentration of thickening agent needed to form an appropriate precursor dope. Samples 9 and 10 were both formed into filaments in the manner described above using a hand syringe. In addition, the dynamic or complex viscosity of the precursor from sample 10 was measured along with the storage and loss moduli. The data are set forth in Tables 2 and 3 and a plot of the data is shown in FIG. 3 of the drawings. Sample 10 was used for this calculation as it appeared to have a viscosity which approached the desired optimum for a viscosity in the shear rate range for producing filaments.

TABLE 1

Weight percentages are given based on the total weight of the microfibrillar cellulose, thickening agent and water.

| Sample | MFC wt % | PEO type List grade used | PEO wt % | H2O wt % |
|---|---|---|---|---|
| 1 | 0.0 | Low | 10.0 | 90.0 |
| 2 | 0.0 | Medium | 4.0 | 96.0 |
| 3 | 0.0 | High | 3.5 | 96.5 |

TABLE 1-continued

Weight percentages are given based on the total weight of the microfibrillar cellulose, thickening agent and water.

| Sample | MFC wt % | PEO type List grade used | PEO wt % | H2O wt % |
|---|---|---|---|---|
| 4 | 5.6 | None | 0.0 | 94.4 |
| 5 | 7.5 | Medium | 3.0 | 89.5 |
| 6 | 3.75 | Medium | 1.5 | 94.75 |
| 7 | 6.8 | None | 0.0 | 93.2 |
| 8 | 5.0 | None | 0.0 | 95.0 |
| 9 | 5.0 | Medium | 3.0 | 92.0 |
| 10 | 7.5 | High | 1.0 | 91.5 |

TABLE 2

Input data for dynamic viscosity, storage modulus and loss modulus data shown in Table 3 below and FIG. 3 of the drawings.
Data Series Information

| | |
|---|---|
| Name: | 7.5% solid 1% PEO FS RT 2 |
| Number of Intervals: | 1 |
| Application: | RHEOPLUS/32 V3.40 21004566-33024 |
| Device: | MCR301 SN80485247; FW3.51D090723; Slot2; Adj19d |
| Measuring System: | CP25-1/TG-SN14155; d = 0.047 mm |
| Accessories: | TU1=CTD450L+R+L-PP/TG-SN80197782-80197782-14 |
| Calculating Constants: | |
| Csr [min/s]: | 5.963509 |
| Css [Pa/mNm]: | 245.5763 |
| Start Delay Time [s]: | 5.491 |
| Substance Density [rho]: | 1,000 |
| Measurement Type: | 0 |
| Motor Correction Factor: | 1 |
| Interval: | 1 |
| Number of Data Points: | 16 |
| Time Setting: | 16 Meas. Pts. |
| Measuring Profile: | Amplitude gamma = 0.2% Angular Frequency omega = 500 . . . 0.5 rad/s log; |Slope| = 5 Pt./dec |

TABLE 3

Data points for complex (dynamic) viscosity, storage modulus and loss modulus shown in FIG. 3 of the drawings.

| Meas. Pts. | Angular Frequency [1/s] | Storage Modulus [Pa] | Loss Modulus [Pa] | Damping Factor [1] | Complex Viscosity [Pa · s] | Deflection Angle [mrad] | Torque [μNm] | Status |
|---|---|---|---|---|---|---|---|---|
| 1 | 500 | 2.11E+05 | 6.23E+04 | 0.295 | 4.39E+02 | 3.49E−02 | 1.78E+03 | TGC, DSO |
| 2 | 315 | 2.05E+05 | 5.98E+04 | 0.292 | 6.76E+02 | 3.49E−02 | 1.72E+03 | TGC, DSO |
| 3 | 199 | 1.99E+05 | 5.70E+04 | 0.286 | 1.04E+03 | 3.49E−02 | 1.68E+03 | TGC, DSO |
| 4 | 126 | 1.87E+05 | 5.37E+04 | 0.287 | 1.55E+03 | 3.51E−02 | 1.58E+03 | TGC, DSO |
| 5 | 79.2 | 1.77E+05 | 5.04E+04 | 0.285 | 2.32E+03 | 3.50E−02 | 1.49E+03 | TGC, DSO |
| 6 | 50 | 1.67E+05 | 4.76E+04 | 0.285 | 3.48E+03 | 3.51E−02 | 1.41E+03 | TGC, DSO |
| 7 | 31.5 | 1.57E+05 | 4.53E+04 | 0.288 | 5.18E+03 | 3.51E−02 | 1.33E+03 | TGC, DSO |
| 8 | 19.9 | 1.50E+05 | 4.29E+04 | 0.286 | 7.83E+03 | 3.50E−02 | 1.26E+03 | TGC, DSO |
| 9 | 12.6 | 1.44E+05 | 4.15E+04 | 0.288 | 1.19E+04 | 3.49E−02 | 1.21E+03 | TGC, DSO |
| 10 | 7.92 | 1.40E+05 | 4.12E+04 | 0.294 | 1.84E+04 | 3.49E−02 | 1.18E+03 | TGC, DSO |
| 11 | 5 | 1.38E+05 | 4.29E+04 | 0.31 | 2.90E+04 | 3.49E−02 | 1.17E+03 | TGC, DSO |
| 12 | 3.15 | 1.41E+05 | 4.61E+04 | 0.326 | 4.72E+04 | 3.48E−02 | 1.20E+03 | TGC, DSO |
| 13 | 1.99 | 1.64E+05 | 6.11E+04 | 0.373 | 8.77E+04 | 3.49E−02 | 1.41E+03 | TGC, DSO |
| 14 | 1.26 | 3.89E+05 | 1.66E+05 | 0.428 | 3.37E+05 | 3.38E−02 | 3.32E+03 | WMa, TGC |
| 15 | 0.792 | 8.16E+05 | 3.84E+05 | 0.471 | 1.14E+06 | 3.40E−02 | 7.11E+03 | WMa, TGC |
| 16 | 0.5 | 1.35E+06 | 7.44E+05 | 0.551 | 3.08E+06 | 3.43E−02 | 1.23E+04 | WMa, TGC |

These and other modifications and variations to the present invention may be practiced by those of ordinary skill in the art, without departing from the spirit and scope of the present invention, which is more particularly set forth in the appended claims. In addition, it should be understood the aspects of the various embodiments may be interchanged either in whole or in part. Furthermore, those of ordinary skill in the art will appreciate that the foregoing description is by way of example only, and is not intended to limit the invention so further described in the appended claims.

What is claimed is:

1. A cellulosic filament precursor dope comprising, based upon the total weight of said precursor dope, from about 7 to about 20 weight percent of microfibrillar cellulose fibers, about 0.2 to about 3 weight percent of a thickening agent and about 75 to about 95 weight percent of a water-based solvent, said microfibrillar cellulose fibers being dispersed in said solvent and said thickening agent being dissolved in said solvent, said precursor dope having a dynamic viscosity ranging from about 400 to about 3000 Pascal seconds at a shear rate of 100 reciprocal seconds.

2. A process for forming a cellulosic filament comprising, mixing a cellulosic textile precursor dope according to claim 1 to a viscosity of about 400 to about 3000 Pa s at a shear rate of 100 reciprocal seconds, extruding said precursor dope into a filament and drying said filament.

3. An absorbent article wherein at least a portion of said article comprises the cellulosic filament of claim 1.

4. The absorbent article of claim 3 wherein said article is selected from the group consisting of a diaper, a diaper pant, a training pant, an incontinence device, a feminine hygiene product, a bandage or a wipe.

5. A process for forming a cellulosic filament nonwoven web comprising, mixing a cellulosic textile filament precursor dope according to claim 1 to a viscosity of about 400 to about 3000 Pa s at a shear rate of 100 reciprocal seconds, extruding said precursor dope into a plurality of filaments, depositing said filaments in a random pattern onto a surface to form a nonwoven web and drying said nonwoven web.

6. The process according to claim 5 which further includes subjecting said nonwoven web to a bonding or entangling process.

* * * * *